United States Patent
Wiley

(10) Patent No.: US 7,153,053 B1
(45) Date of Patent: Dec. 26, 2006

(54) DISPENSER FOR LIP COLORING AND COATING FLUIDS

(76) Inventor: Lien L. Wiley, 2164 Brownstone Creek Ave., Simi Valley, CA (US) 93063

( * ) Notice: Subject to any disclaimer, the term of this patent is extended or adjusted under 35 U.S.C. 154(b) by 111 days.

(21) Appl. No.: 10/989,804

(22) Filed: Nov. 17, 2004

(51) Int. Cl.
*B43M 11/02* (2006.01)

(52) U.S. Cl. .................................. 401/219; 401/208

(58) Field of Classification Search .............. 401/208, 401/219, 220, 281, 218
See application file for complete search history.

(56) References Cited

U.S. PATENT DOCUMENTS

| 3,256,550 A | * | 6/1966 | Laxalt | 401/141 |
| 5,785,063 A | * | 7/1998 | DePinto | 132/200 |
| 6,126,352 A | * | 10/2000 | Wiley | 401/208 |
| 6,196,743 B1 | * | 3/2001 | Brucker | 401/6 |
| 6,948,876 B1 | * | 9/2005 | De Laforcade | 401/220 |

* cited by examiner

*Primary Examiner*—Justine Yu
(74) *Attorney, Agent, or Firm*—Allen A. Dicke, Jr.

(57) ABSTRACT

Fluid material, including medication, dermatological fluids, cream eye shadow and lip-coloring material such as lip gloss, is stored in a reservoir. Rotating a collar with respect to the reservoir advances a piston therein to deliver lip coloring or other material through a valve to a roller mounted on a dispensing head.

15 Claims, 5 Drawing Sheets

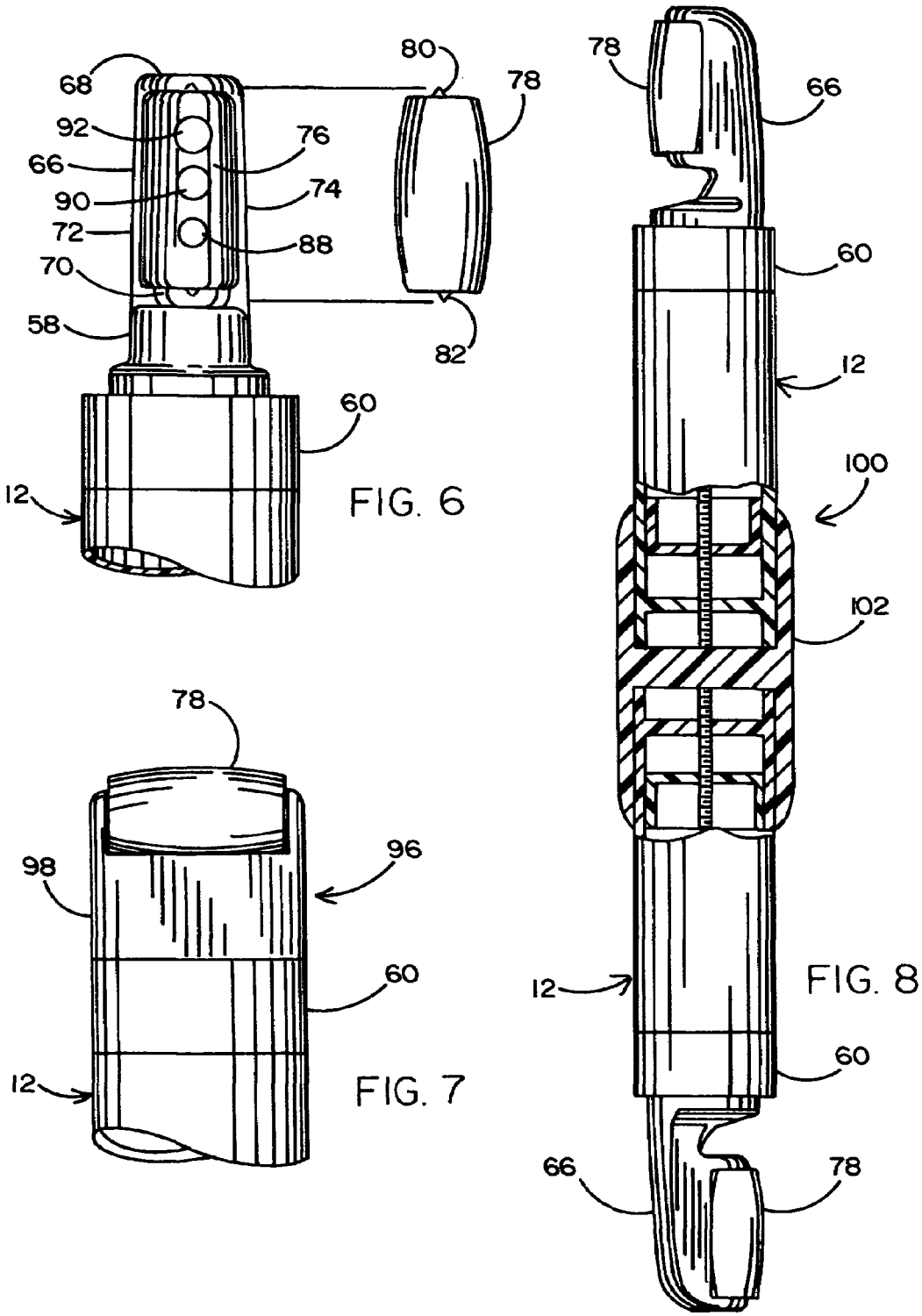

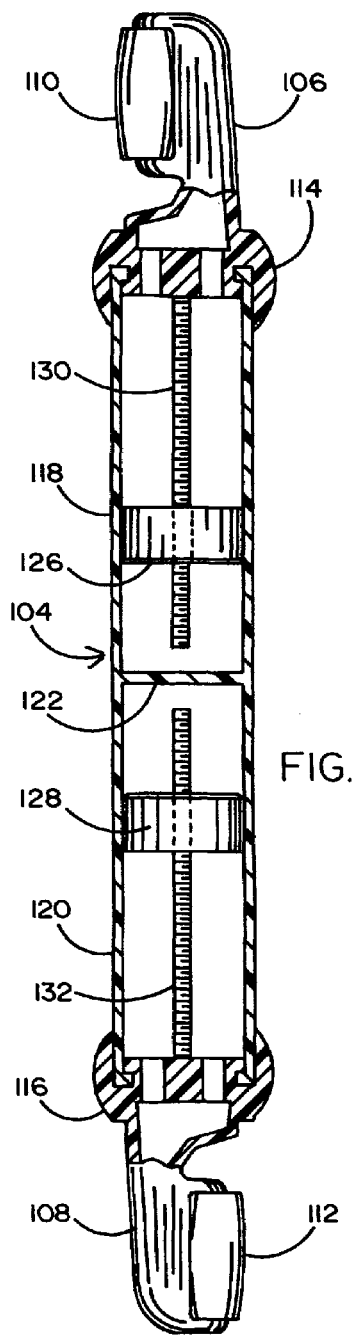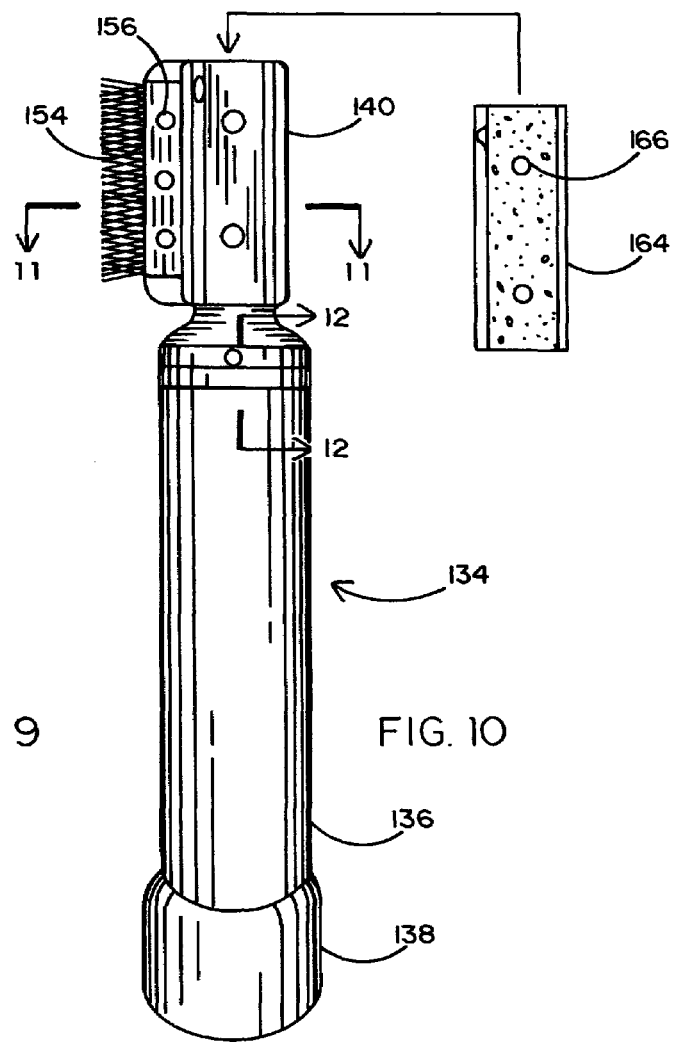

DISPENSER FOR LIP COLORING AND COATING FLUIDS

BACKGROUND OF THE INVENTION

Lipstick is utilized by many women as an important part of their makeup to enhance their appearance. The conventional lipstick is in the form of a hard paste which is sufficiently firm to be self-supporting. The most commonly employed lipstick is mounted on a base in a lipstick tube. The base can be advanced so that the portion of the lipstick extending from the tube can be applied to the lips. Many colors are available.

It appears that the glossiness of the applied lipstick is limited by the hard paste structure of the lipstick. When the lip coloring material is of a lower viscosity so that it is not self-supporting, greater glossiness can be achieved. Fluid lip coloring is available and is applied by brush. Brush application is difficult and is very different than the application of the hard lipstick. Thus, it is a different experience and requires different manual skills.

Applying lip coloring by means of a roller permits the utilization of lip coloring material which is of lower viscosity than the hard paste. Roller-applied lip coloring can be a gel. With the proper applicator device, the lip coloring can enjoy the gloss which is possible with lower viscosity, but can also be dispensed with a roller so that it utilizes most of the physical dexterity learned by applying the usual hard paste lipstick. In addition to lip coloring, various other fluids need to be carefully placed. These include medicines, dermatological products, medicines for inside of the mouth, cream eye shadow and similar products. Thus, there is a need for a roller dispenser particularly configured for the application of viscous gel lip coloring material.

SUMMARY OF THE INVENTION

To aid in the understanding of this invention, it can be stated in essentially summary form that it is directed to a lip-coloring dispenser. The dispenser has a cylindrical reservoir with a piston therein. The piston is driven to deliver viscous gel lip coloring, preferably through a valve, to a roller-dispensing head. The roller is rotatably mounted in the head and receives the lip-coloring material from the head. The roller is rotated by motion along the lips to which the coloring is to be applied. Other similar products, like medicines, dermatological products, medicines for inside and around the mouth or cream eye shadow can be applied. In this way, coloring is applied utilizing the same dexterity as the conventional lipstick.

It is a purpose and advantage of this invention to provide a lip-coloring and coating dispenser which has a reservoir in which the viscous gel lip coloring is stored, together with structure to deliver the lip-coloring material to a roller on the dispenser. Rolling the roller along the lips applies the lip coloring thereto.

It is another purpose and advantage of this invention to provide a lip-coloring dispenser which is configured so that it can apply a viscous gel lip-coloring material using the dexterity which is utilized in applying hard liquid material.

It is a further purpose and advantage of this invention to provide a lip-coloring dispenser which is easy to use and which has a valve therein so that the lip coloring can be conserved.

It is a further purpose and advantage of this invention to provide a double-ended lip-coloring dispenser wherein two reservoirs are secured together, with dispensers on opposite ends so that two lip-coloring materials can be handled at the same time.

Other purposes and advantages of this invention will become apparent from a study of the following portion of the specification, the claims and the attached drawings.

BRIEF DESCRIPTION OF THE DRAWINGS

FIG. 6 is a front view of the lip-coloring dispenser of FIG. 1, with parts broken away, and showing the roller in projected position.

FIG. 7 is a side elevational view of a second preferred embodiment of the lip-coloring dispenser, which is the same as the lip-coloring dispenser of FIG. 1, with the axis of the roller at a right angle to the axis of the dispenser.

FIG. 8 is a side-elevational view, with parts broken away, showing a third preferred embodiment wherein two of the lip-coloring dispensers of FIG. 1 are joined together, base to base, with one dispenser operator.

FIG. 9 is a longitudinal section through a fourth preferred embodiment of the lip-coloring dispenser of this invention, showing two of the dispensers fixed together base to base with separate dispenser operators.

FIG. 10 is a side-elevational of the dispenser which includes a brush and a pad so that the applied material, lip-coloring material or other, can be brushed on and wiped smooth.

DESCRIPTION OF THE PREFERRED EMBODIMENTS

Figure 1:
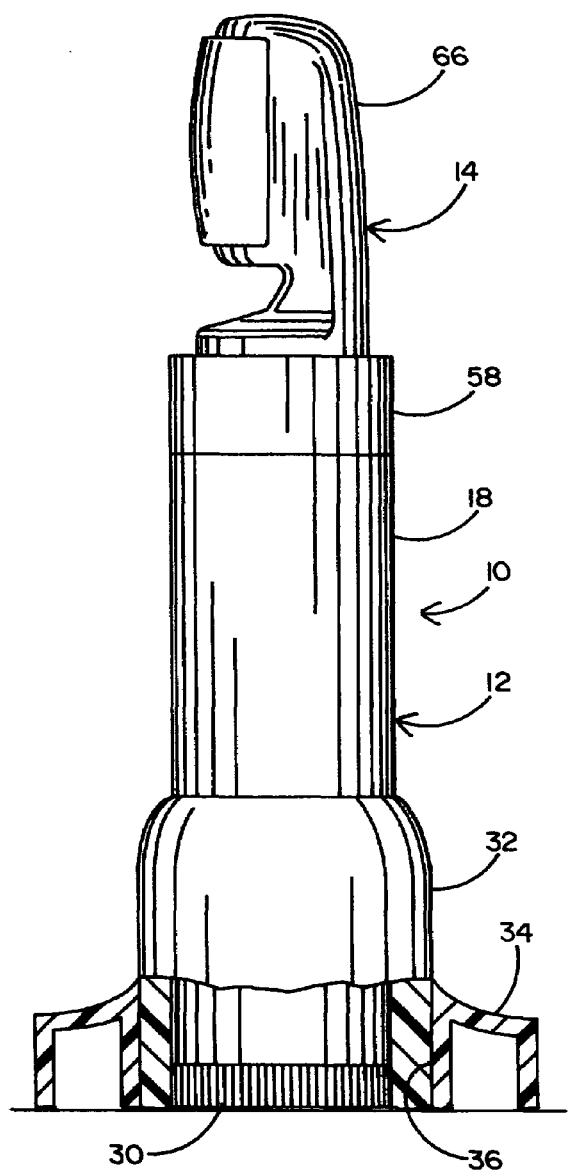
FIG. 1 is a side-elevational view of the first preferred embodiment of the lip-coloring dispenser of this invention, with parts broken away and parts taken in section.

The first preferred embodiment of the lip-coloring dispenser of this invention is generally indicated at 10 and is seen in FIGS. 1, 2, 3, 4 and 5. The dispenser 10 has a reservoir 12 and a dispensing head 14. First considering the reservoir, it is in the configuration of a right circular tube having an inside wall 16 and an outside wall 18. Piston 20 lies within the reservoir tube and is generally in the configuration of an upwardly facing cup. It has a screw-threaded opening 22 in its center. Lead screw 24 is threaded into the opening of the piston.

The reservoir has a bottom wall 26 through which the lead screw extends. The lead screw carries a shoulder 28 on the inside of the bottom wall 26. Dial 30 is attached or is integrally formed with the lead screw below the shoulder 28. The lead screw is thus permitted to rotate, but cannot move axially within the reservoir. Dial 30 is cup-shaped and has a circular wall 32 which extends upward a portion of the way up the outside wall 18.

Figure 2:
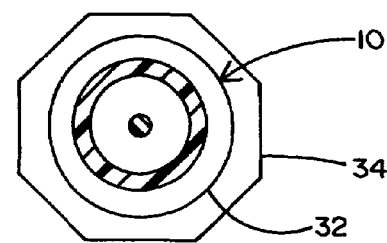
FIG. 2 is a downward looking sectional view through the lip-coloring dispenser showing one configuration of the base in plan view.
Figure 3:
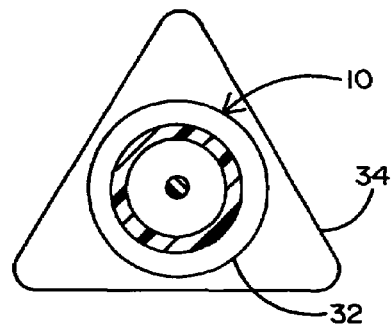
FIG. 3 is a similar view, showing another configuration of the base in plan view.
Figure 4:
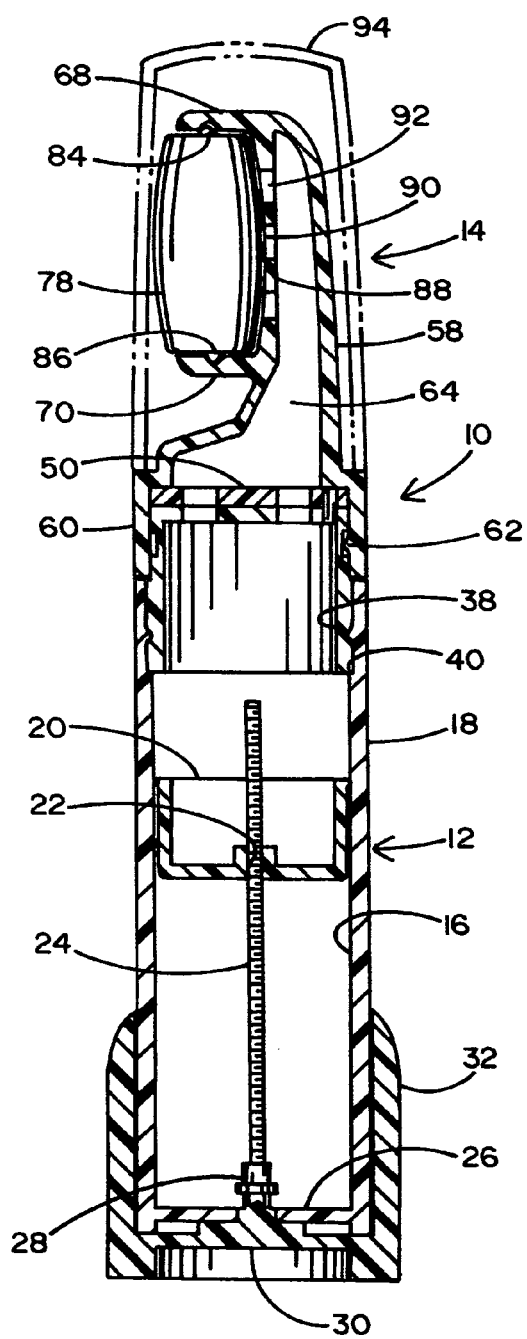
FIG. 4 is a longitudinal section through the lip-coloring dispenser of FIG. 1, showing the cap in phantom lines.
Figure 5:
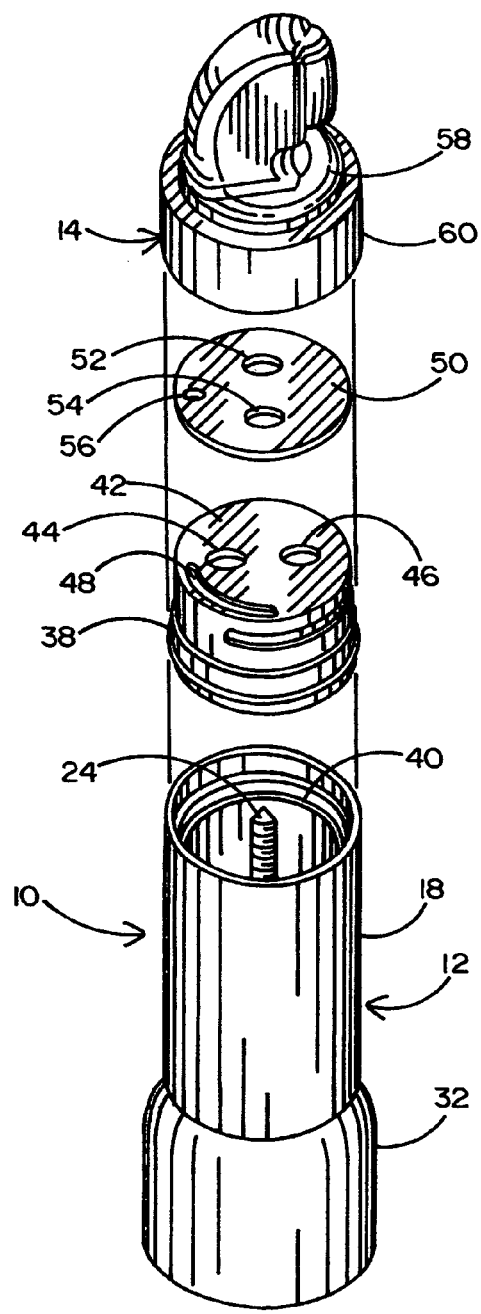
FIG. 5 is an exploded view of the lip-coloring dispenser of FIG. 4.

The lip-coloring dispenser 10 is quite small. In order to aid in its standing upright, base 34 is provided. The base has an interior opening 36 which is sized to releasably receive the wall 32 of the dial 30. The plan outline of the base may be circular; it may be octagonal, as seen in FIG. 2; or it may be triangular, as seen in FIG. 3. The dispenser can be removed from the base for use and can be reinstalled in the base after use to maintain the dispenser in the upright position. Any convenient configuration or size of the base will provide this function.

The dispensing head 14 is rotatably mounted on the reservoir to control a valve. The valve controls the flow of gel lip coloring material from the reservoir into the dispensing head. Tubular valve body 38 is inserted into the top of the reservoir tube and engages against the shoulder 40 therein. The valve body 38 is in the form of an inverted cup. The top wall 42 of the inverted cup has two fluid passage openings 44 and 46. It also has arcuate slot 48. The valve body is fixed into the top of the reservoir. Lying on top of the valve body is valve disc 50. The valve disc 50 has two openings 52 and 54 which are also eccentric. The holes 52 and 54 are in alignment with the holes 44 and 46 when the valve is in the open position shown in FIG. 4 and are out of alignment in the closed position shown in FIG. 5. Pin 56 is formed on the bottom of valve disc 50 and engages in slot 48 to limit rotation of the disc 50 with respect to the valve body 38.

Dispensing head 14 has a housing 58 which includes a collar 60. The collar 60 has a ridge 62, see FIG. 4, which snaps into a corresponding groove in the valve body 38. This permits rotation of the dispensing head on the valve body. The valve disc 50 is fixed into the collar 60 against the shoulder in the housing 58. The housing 58 has an interior passage 64 which receives lip coloring fluid material when the valve is open and the piston 20 is moved upward.

The housing 58 extends upward as a narrow finger 66. It has top end wall 68 and bottom end wall 70, see FIGS. 4 and 6. These end walls and low sidewalls 72 and 74, see FIG. 6, define a basket 76. The basket receives roller 78, which is in the form of an oblate spheroid with truncated ends. The truncated ends carry pivot pins 80 and 82, see FIG. 6, which engage in pivot sockets 84 and 86, see FIG. 4. The pivot pins are preferably pointed conical structures, and the pivot sockets are preferably conical sockets with a larger conical angle to limit contact to near the points. In this way, the roller can roll within the basket.

The basket has passages 88, 90 and 92 through the bottom basket wall into the interior passage 64. The lip-coloring material dispenser 10 is normally used in the upright position. In order to deliver equal amounts of lip-coloring material over the height of the roller, the dispensing passages 88, 90 and 92 are progressively larger, as seen in FIG. 6. The size of these passages and the progression of larger sizes from bottom to top is a function of the spacing between the passages and the viscosity of the lip-coloring material. The lip-coloring fluid material is delivered onto the back of the roller in the basket. Cap 94 is preferably a clear polymer cap and can be installed over the dispensing head when not in use. This protects the material on the roller from inadvertently contacting the wrong surface and reduces drying out of the material. Of course, in the storage position, the valve disc 50 is in the closed position.

FIG. 7 is a side-elevational view, with the lower end broken away, of the lip-coloring dispenser 96. The dispenser 96 is very similar to the dispenser 10. It has the same reservoir structure with a piston therein. It has the same piston advance mechanism. The housing 98 has the same collar 80 with a valve therein. The housing 98 is configured so that the roller 78 rotates on an axis which is at a right angle with respect to the axis of the reservoir. This illustrates that the roller is useful at any angle between the angle of FIG. 6 and the angle of FIG. 7.

FIG. 8 illustrates the lip-coloring dispenser 100, which is formed of two reservoirs 12, each carrying a dispensing structure including a shutoff valve and a dispensing head with dispensing roller. In this case, the dispensing dial 102 extends in cuplike configuration to embrace the screw end of each reservoir. The screws are each attached to the dispensing ring so that when either the upper or the lower reservoir is turned with respect to the dispensing ring, that piston is advanced. In this way, two different lip-coloring materials can be carried together. They can be different colors for stylized appearance or they can be a basic lip-coloring gloss material and a clear super-gloss covering material. The dispenser 100 places both receptacles conveniently at hand.

FIG. 9 illustrates a lip-coloring dispenser 104 which is a double dispenser similar to the one disclosed in FIG. 8. FIG. 9 is a substantially central longitudinal section, except that the dispensing fingers 106 and 108 are in side-elevation. The dispensing fingers respectively carry rollers 110 and 112, which are mounted the same way as the roller 78 in FIG. 6. The fingers are mounted on housings which include collars 114 and 116. The reservoirs 118 and 120 are the same right circular cylindrical tubes separated by wall 122. The wall 122 maintains the lip-coloring material separate in the two reservoirs. The reservoirs respectively have pistons 126 and 128 mounted on piston drive screws 130 and 132. The piston drive screws are respectively attached to the collars 114 and 116. Thus, when the collar 114 is rotated with respect to the reservoir tube, the piston 126 is driven upward to push lip-coloring material up through the openings in the collar and into the dispensing finger 106. From there, it is delivered through the openings in the finger to the roller from which it is applied to the lips. When the collar 116 is rotated with respect to the reservoir tube, the piston 128 forces the lip-coloring material into reservoir 120 out through finger 108 to the roller 112. Thus, the two lip coloring materials are conveniently at hand and can be individually dispensed.

Figure 11:
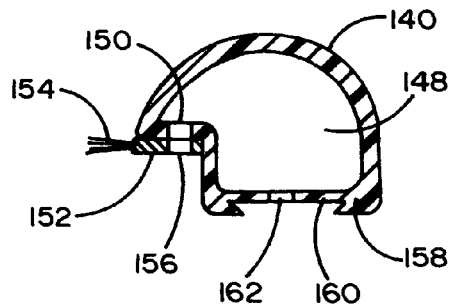
FIG. 11 is an enlarged section taken generally along the line 11—11 of FIG. 10.
Figure 12:
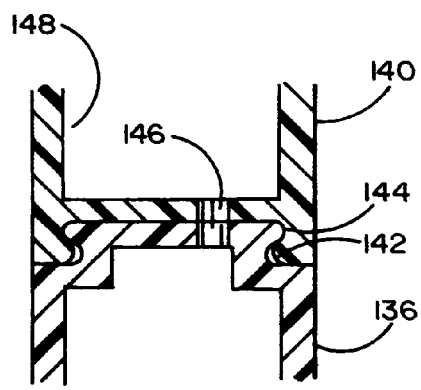
FIG. 12 is a sectional view taken generally along the line 12—12 of FIG. 5, with parts broken away, showing the valving structure.

Dispenser 134 is shown in side-elevational view in FIG. 10. Enlarged details thereof are shown in FIGS. 11 and 12. The dispenser 134 has a reservoir 136. Collar 138 which is rotatable on the lower end of the reservoir drives a screw which drives the piston upward in the reservoir the same as the structure shown in FIG. 4. The dispensing head 140 has an inwardly-facing ring 142 which snaps over a corresponding ring 144 on the reservoir, see FIG. 12. These rings provide rotatability of the dispensing head on the reservoir. This rotatability provides dial valving action by means of eccentric holes 146. The holes are in alignment in FIG. 12. Rotation of the dispensing head 140 on the reservoir 146 moves the holes out of alignment to result in closure of the reservoir. The dispensing head 140 has a lip coloring material space 148 therein. Material in the reservoir is delivered into the space in the dispensing head when the valve dial is opened and the collar 138 is turned.

The dispensing head has two flats on it, see FIG. 11. Flat 150 carries a brush base 152 which carries brush bristles 154 thereon. Dispensing openings 156 extend through the flat 150 and brush base so that lip coloring material in the space in the dispensing head can flow out adjacent the brush.

Material is dispensed out of the openings 156 and is spread with the bristles of the brush.

In addition, the head has a flat 158 in which is formed as a female dovetail 160. Opening 162 permits material in the space 148 to move out into the dovetail. Pad 164, see FIG. 10, is shaped to be inserted into the dovetail from the top. The pad is a felted or woven pad. It also receives the fluid from the space 148. When the pad is not densely formed, the interstices therein are sufficient to permit the fluid to flow out through the pad. If the pad material is dense, openings 166, in line with the openings 162, may be necessary to permit the delivery of the material.

Figure 13:
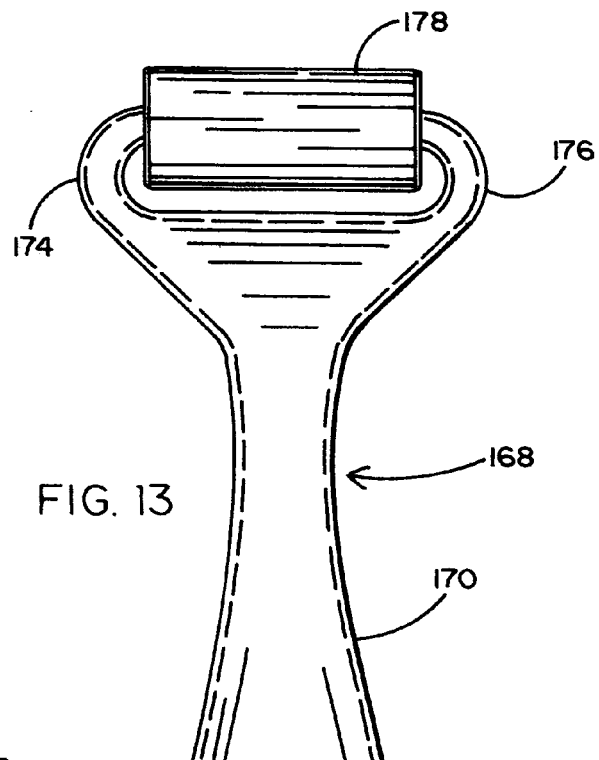
FIG. 13 is a side-elevational view of another embodiment of the lip-coloring dispenser of this invention.
Figure 14:
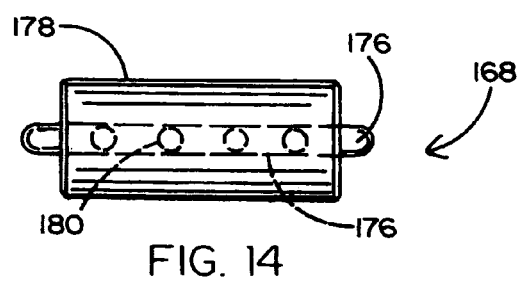
FIG. 14 is a top view thereof.

Dispenser 168 is illustrated in FIGS. 13 and 14. Reservoir 170 is a flexible thin wall reservoir made of polymer material. It has a cap 172 at its lower end to permit filling of the reservoir. The material filled therein is a beauty aid such as lip gloss. Lip gloss is fluid with a viscosity between water and thick cream. The upper end of the reservoir is bifurcated to form two yoke arms 174 and 176. The yoke arms extend toward each other and form a pintle 176 upon which roller 178 is mounted. The pintle, shown in dashed lines in FIG. 14, has openings 180 therein which permit delivery of the fluid material from the reservoir into the roller 178. The roller 178 is made of porous material such as open-cell foam rubberlike material. Thus, when the reservoir is squeezed, the fluid material is delivered to the inside of the roller. Manual rolling of the roller across the surface to which the material is to be applied delivers the material through the roller onto the surface. The material is preferably lip gloss material which is rolled onto the lips.

This invention has been described in its presently preferred embodiment, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A lip-coloring dispenser comprising:
    a reservoir for containing lip-coloring material, said reservoir having an outlet end, said reservoir being tubular and having a piston therein, structure to move said piston toward said outlet end to move lip-coloring material toward said outlet end;
    a dispenser housing mounted on said reservoir at said outlet end of said reservoir, a dispensing roller rotatably mounted on said dispenser housing and a plurality of openings in said dispensing head to deliver lip-coloring material to said roller, said plurality of openings being of progressively larger size in a direction away from said reservoir so that material can be delivered through said dispenser housing and deposited on said roller so that said roller can roll on said lip-coloring material.

2. The lip-coloring dispenser of claim 1 wherein there is a valve between said reservoir and said dispenser housing.

3. The lip-coloring dispenser of claim 2 wherein said valve comprises a rotary valve wherein said reservoir carries a first opening and said dispenser housing carries a second opening, with said dispenser housing being movable with respect to said reservoir to move said openings into and out of alignment to respectively open and close said valve.

4. The lip-coloring dispenser of claim 3 wherein said valve in said reservoir comprises a plate on a body, said body being inserted into said reservoir.

5. The lip-coloring dispenser of claim 4 wherein said housing carries a second valve plate, said second valve plate being attached to said dispenser housing so that it rotates with respect to said reservoir to move said openings into and out of alignment.

6. The lip-coloring dispenser of claim 5 wherein there is a lead screw threaded into said piston so that rotation of said lead screw advances said piston in said reservoir.

7. The lip-coloring dispenser of claim 6 wherein there is a dispensing ring embracing said reservoir and rotatable with respect to said reservoir, said lead screw being connected to said dispensing ring so that said dispensing ring can be manually rotated with respect to said reservoir.

8. The lip-coloring dispenser of claim 7 wherein said lead screw defines an axis and said reservoir is a circular tube having said axis as the centerline, said roller being rotatably mounted on a roller axis which is parallel to said screw axis.

9. The lip-coloring dispenser of claim 7 further including a base, said base being larger than said dispensing ring, said base having an opening therein sufficiently large to receive said dispensing ring so that said lip-coloring dispenser can be removably inserted into said base to aid in retaining said lip-coloring dispenser in an upright position.

10. The lip-coloring dispenser of claim 1 wherein there is a lead screw threaded into said piston so that rotation of said lead screw advances said piston in said reservoir.

11. The lip-coloring dispenser of claim 10 wherein said lead screw defines an axis and there is a ring embracing said reservoir and rotatable with respect to said reservoir, said lead screw being connected to said ring so that said ring can be manually rotated with respect to said reservoir.

12. The lip-coloring dispenser of claim 11 wherein said reservoir is a circular tube having said axis as the centerline, said roller being rotatably mounted on a roller axis which is parallel to said screw axis.

13. The lip-coloring dispenser of claim 11 wherein said roller axis is at a right angle to said screw axis.

14. The lip-coloring dispenser of claim 11 wherein there are first and second of said reservoirs and said dispensing ring engages around a portion of each of said first and second reservoirs to retain said reservoirs in a position wherein said dispenser heads are away from each other so that rotation of said first reservoir with respect to said dispensing ring delivers lip coloring material to said first roller and rotation of said second reservoir with respect to said dispensing ring delivers lip-coloring material to said second roller.

15. The lip-coloring dispenser of claim 1 wherein there are first and second of said reservoirs and said structure to move said piston includes a dispensing ring and said dispensing ring engages around a portion of each of said first and second reservoirs to retain said reservoirs in a position wherein said dispenser heads are away from each other so that rotation of said first reservoir with respect to said dispensing ring delivers lip coloring material to said first roller and rotation of said second reservoir with respect to said dispensing ring delivers lip-coloring material to said second roller.

* * * * *